(12) United States Patent
Gasquez et al.

(10) Patent No.: US 12,040,095 B2
(45) Date of Patent: Jul. 16, 2024

(54) SYSTEM AND METHOD FOR TABLING MEDICAL SERVICE PROVIDER DATA PROVIDED IN A VARIETY OF FORMS

(71) Applicant: MDX Medical, Inc., Lyndhurst, NJ (US)

(72) Inventors: Emmanuel A. Gasquez, Franklin, MA (US); Nicholas J. Byra, Hudson, MA (US)

(73) Assignee: MDX Medical, LLC, Lyndhurst, NJ (US)

( * ) Notice: Subject to any disclaimer, the term of this patent is extended or adjusted under 35 U.S.C. 154(b) by 553 days.

(21) Appl. No.: 14/293,918

(22) Filed: Jun. 2, 2014

(65) Prior Publication Data
US 2015/0348218 A1 Dec. 3, 2015

(51) Int. Cl.
  *G16H 70/00* (2018.01)
  *G06Q 10/10* (2023.01)

(52) U.S. Cl.
  CPC ............ *G16H 70/00* (2018.01); *G06Q 10/10* (2013.01)

(58) Field of Classification Search
  CPC ........ G06Q 50/22; G06Q 50/24; G06Q 10/10; G06F 19/30; G06F 19/32; G06F 19/321; G06F 19/34; G16H 70/00
  USPC ...................................................... 705/2, 3
  See application file for complete search history.

(56) References Cited

U.S. PATENT DOCUMENTS

| | | | | |
|---|---|---|---|---|
| 6,292,771 | B1* | 9/2001 | Haug | G06F 40/216 704/9 |
| 7,844,472 | B1* | 11/2010 | Akin | G06Q 10/06 705/2 |
| 9,691,075 | B1* | 6/2017 | Ray | G06Q 10/10 |
| 2003/0036683 | A1* | 2/2003 | Kehr | G16H 50/20 600/300 |
| 2005/0114277 | A1* | 5/2005 | Russell | G06F 16/903 706/12 |
| 2005/0192792 | A1* | 9/2005 | Carus | G06F 40/30 704/2 |

(Continued)

OTHER PUBLICATIONS

Andy Oppel, Database: A Beginner's Guide, The McGraw-Hill Companies, 73 pages (Year: 2009).*

(Continued)

*Primary Examiner* — Jason S Tiedeman
(74) *Attorney, Agent, or Firm* — Leydig, Voit & Mayer, Ltd.

(57) ABSTRACT

A system is described for rendering normalized medical service provider data records by transforming received input records from a variety of sources into standardized medical service provider data records. The system digests a resource containing multiple data points to render a mapping between individually identifiable parts of the data points and normalized data types handled by data type-specific parsers. A matching operation is performed, on parsed data points, wherein individual ones of the set of parsed data points are matched to an identified entry on an authoritative listing. During the matching an algorithmic match is attempted by assigning a match score based upon a type of transformation on a parsed data point value, of a data point instance of the set of parsed data points, to render a match between the parsed data point value and an entry within an authoritative data listing.

20 Claims, 5 Drawing Sheets

(56) References Cited

U.S. PATENT DOCUMENTS

| | | | |
|---|---|---|---|
| 2008/0046292 A1* | 2/2008 | Myers | G06F 16/283 |
| | | | 705/3 |
| 2009/0099865 A1* | 4/2009 | Zak | G16H 40/20 |
| | | | 705/2 |
| 2009/0319521 A1* | 12/2009 | Groeneveld | G06F 16/951 |
| 2010/0017227 A1* | 1/2010 | Kivatinetz | G16H 10/60 |
| | | | 705/3 |
| 2011/0004488 A1* | 1/2011 | Benja-Athon | G16H 50/20 |
| | | | 707/769 |
| 2012/0197631 A1* | 8/2012 | Ramani | G06F 40/268 |
| | | | 704/9 |
| 2013/0268440 A1* | 10/2013 | Tierney | G06Q 20/10 |
| | | | 705/44 |
| 2014/0046696 A1* | 2/2014 | Higgins | G16B 40/00 |
| | | | 705/3 |
| 2014/0095209 A1* | 4/2014 | Molny | G16Z 99/00 |
| | | | 705/3 |
| 2014/0156228 A1* | 6/2014 | Molettiere | G06F 19/322 |
| | | | 702/189 |
| 2014/0164564 A1* | 6/2014 | Hoofnagle | H04L 67/125 |
| | | | 709/217 |
| 2014/0200920 A1* | 7/2014 | Malec | G06Q 10/10 |
| | | | 705/3 |
| 2015/0188872 A1* | 7/2015 | White | H04L 51/28 |
| | | | 709/206 |
| 2015/0199744 A1* | 7/2015 | Tolvanen | G06Q 30/0631 |
| | | | 707/737 |

OTHER PUBLICATIONS

Allen G. Taylor, SGL for Dummies, Wiley Publishing, Inc., 41 Pages (Year: 2003).*

Gilleland et al., Levinshtein Distance, in Three Flavors, http://people.cs.pitt.edu/~kirk/cs1501/Pruhs/Spring2006/assignments/editdistance/Levenshtein%20Distance.htm, 11 pages (Year: 2013).*

Kleiweg, Levenshtein algorithm, www.let.rug.nl/~kleiweg/lev/levenshtein.html, 3 pages (Year: 2013).*

* cited by examiner

| # | Field |
|---|---|
| 302 | Actions (legal) |
| 304 | Address Insurance |
| 306 | Certifications |
| 308 | Credentials |
| 310 | Dates |
| 312 | Expertise |
| 314 | Hospitals |
| 316 | Hours |
| 318 | Image |
| 320 | Insurance (General Info) |
| 322 | Language |
| 324 | Licenses |
| 326 | Names |
| 328 | Phones |
| 330 | Practice Names |
| 332 | Provider (personal information) |
| 334 | Schools |
| 336 | Specialities |
| 338 | Training |
| 340 | Associations |

FIG. 3

SYSTEM AND METHOD FOR TABLING MEDICAL SERVICE PROVIDER DATA PROVIDED IN A VARIETY OF FORMS

FIELD OF THE INVENTION

This invention relates generally to the field of database building and maintenance. More particularly, the invention is directed to rendering normalized database records from input provided in the form of aggregated data sets relating to medical service providers.

BACKGROUND OF THE INVENTION

In recent years there has been a proliferation of searchable data available to the general public via the Internet. The area of medical service providers is no exception. Today, users can go on line and submit search requests relating to a wide variety of medical services, and receive a variety of resulting search results. For example, a user can access a medical service provider search site and enter a variety of search parameter values including, for example: a medical service provider type, a geographic region, and a variety of personal preferences. A search engine operating in association with the search site applies search parameter values specified by the user to a database comprising information for a population of medical service providers represented by data record contents of a medical service provider database.

People generally place a high degree of value on their health. When a person needs to consult a medical service provider for a particular type of medical service or ailment, there must be a high level of confidence that the medical service provider meets the needs and/or expectations of the patient. The challenge for a medical service provider search site is therefore to instill a high level of confidence that a listing of service providers returned in search results provided by the medical service provider search site, for a particular user query, accurately represents the population of available service providers of primary interest to the requestor.

Thus, the value of such medical service provider search sites, to the requestor, is highly dependent upon the quality and the quantity of the information within the tables maintained within the databases used by the service provider search engine. There must be a sufficient quantity of service providers represented in the databases. For example, if only a small percentage of available service providers are represented in the database records, then users will eventually realize that the sample size is insufficient to provide confidence that a desired medical service provider can be identified from a search submitted via the search site since many other service providers weren't even considered by the search. Similarly, if the information contained in the database itself is inaccurate, then one should not be expected to place a high degree of confidence or trust in the provided results.

There exists a wide variety of highly desirable data available to the general public relating to medical service providers. Such information is both accurate and covers most of the medical service provider population. However, the data is not provided from a single source and is not provided in a single form. Thus, a vast quantity of potentially highly valuable medical service information is underutilized because it simply cannot be accessed (e.g. searched) and presented to interested persons in a meaningful way.

When building a comprehensive database of medical service provider information, the source information for such database may come from hundreds of independent sources. Moreover, such sources may be of many types including, for example, a data scrape from a hospital's website, directly provided records from insurance company databases, a data scrape from a medical insurance provider website, data provided by/for an individual group practice, individual self-provided provider data from individual service providers, etc. Such data is arranged and packaged in a variety of forms/formats including, for example, Microsoft Access (MDB), extensible markup language (XML), comma separated values (CSV), etc.

The fields of data within each received package of data, in general, depend on the way the information is obtained. In the case of database records provided in an agreed format by a particular source, the data fields of the records likely contain the proper type of data within identified fields. For example, a provider of records in a set format provides a record wherein an address field includes (per agreement or previous notice) a street, suite/apt, city, state, and zip. However, when input data arises from a data scrape from a website, the recipient of the scraped input data is left to determine a layout of the individual HTML content of the scraped website content. Such scraped content, in the case of address information, may be provided in the form of an address containing identified data fields. In other cases, scraped address data may be presented as a blob of unlabeled data strings. Also, the information provided in a data scrape may not accurately label the provided data fields. In other cases, a portion of the provided data may be properly labeled while other parts are mislabeled—even single pieces of data.

The absence of regularity and/or high reliability of medical service provider data acquired from a wide variety of sources raises substantial barriers to providing comprehensive reliable data for medical service providers from publicly accessible sources.

SUMMARY OF THE INVENTION

Embodiments of the invention are used to provide a system and method for rendering normalized data records from a variety of input data sets. In particular, a method is described herein for transforming received input medical service provider data records from a variety of medical service provider data sources into standardized medical service provider data records for storage on a medical service provider database. The method includes importing a received resource containing multiple data points. During the importing, the received resource is digested to render a mapping between individually identifiable parts of the multiple data points and normalized data types handled by a parser of a set of data type-specific parsers.

The method further comprises designating, based upon the mapping during the importing, one of the data type-specific parsers for each of the multiple data points. Thereafter, the method includes parsing the multiple data points using a designated one of the set of data-type specific parsers to render a set of parsed data points. Thereafter, a matching is performed wherein individual ones of the set of parsed data points are matched to an authoritative data listing entry. During the matching an algorithmic match is attempted by assigning a match score based upon a type of transformation on a parsed data point value, of a data point instance of the set of parsed data points, to render a match between the parsed data point value and an entry within the authoritative data listing. Transformations of the parsed data point value that match an entry of the authoritative database to render a set of transformation match scores are scored.

The method continues by determining a transformation of the parsed data point value having a highest scoring transformation match of the set of transformation match scores to render a winning parsed data point value. Thereafter, the method includes exporting the winning parsed data point value to a database of processed medical service provider data.

The illustrative examples furthermore include a non-transitory computer-readable medium including computer-executable instructions for configuring a computer system, including a processor, to execute the above-summarized operations. Illustrative examples furthermore include a computer system including a programmed processor and a computer-readable medium containing computer-executable instructions that, when executed by the programmed processor, carry out the summarized operations recited above.

BRIEF DESCRIPTION OF THE DRAWINGS

While the appended claims set forth the features of the present invention with particularity, the invention and its advantages are best understood from the following detailed description taken in conjunction with the accompanying drawings, of which:

FIG. 3 summarizes an exemplary set of parsers incorporated into the rendering facility;

DETAILED DESCRIPTION OF THE DRAWINGS

The figures and associated written description provide illustrative examples of a data normalization facility for rendering normalized data for storage as records in tables of a database accessed by a medical service provider search engine accessed via a medical service provider search site.

Figure 1:
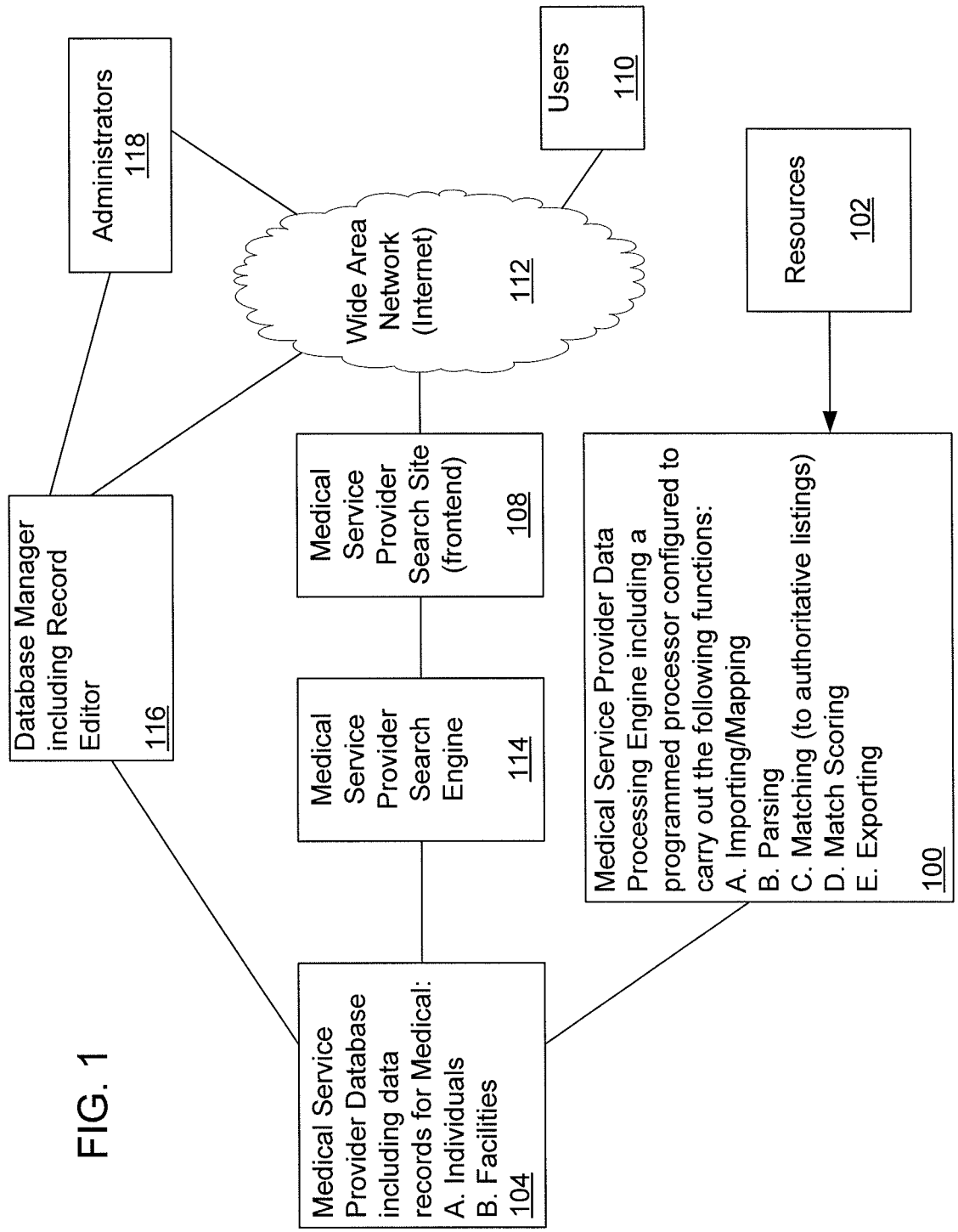
FIG. 1 is a schematic diagram illustrating a networked environment wherein a data normalization facility is provided to render normalized data for storage as records in tables of a database accessed by a medical service provider search engine accessed via a medical service provider search site.

Turning to FIG. 1, a schematic diagram depicts functional/structural components of an exemplary networked system suitable for carrying out embodiments of the system and method described herein for rendering normalized data for storage as records in tables of a database accessed by a medical service provider search engine accessed via a medical service provider search site. In particular, the system includes a medical service provider data processing engine 100 that carries out operations upon received resources 102 (raw input data sets). A "resource", as used herein, is a specific batch (iteration) of input data from a data source. Each resource, when received by the medical service provider data processing engine 100, is received in a substantially regular form that is known by the processing engine 100. As noted above, the contents of any particular "resource" instance may vary substantially in form from other received resource instances. Such variance in form arises from the wide variety of input data sources providing instances of the resources 102 (e.g. a data scrape from a particular hospital's web site, insurance company records, licensing organization databases, etc.). Such variances also arise from changes, such as changes in the types of information, from a same source over the course of time.

The data processing engine 100 is configured to include a computer-readable medium including computer-executable instructions for carrying out the functions of: importing/mapping, parsing, matching, scoring (assigning a degree of confidence grade to the matching operation result), and exporting (to tables for access by the medical service provider search engine). Each of these functions is described herein below with reference to FIGS. 2-4. As such the data processing engine 100 extracts data from raw input provided by the resources 102, transforms the extracted data into normalized data record content, and then loads the normalized data to a medical service provider database 104 that includes data tables relating to both individuals (e.g. medical professionals) and facilities (e.g., hospitals). The data processing engine 100 receives real-world data in a variety of formats and relates the data to medical service providers represented in the service provider database 104.

A medical service provider search site 108 includes a medical service provider search page. The medical service provider search page includes a set of search fields through which users 110 specify search queries. The users 110 access the search site 108 via a wide area network 112. The search queries, specified via the search site, are executed by a medical service provider search engine 114 configured to access the contents of the service provider database 104 and render responsive search results. The results are provided to the users 110 via the search site 108. Thus, in general, the normalized data rendered by the data processing engine 100, then stored in the medical service provider database 104, is usable by a variety of medical service provider search sites offering search services to a variety of user types.

Additionally, a database manager 116 is configured to access tabled content of the medical service provider database. The database manager 116 is accessed by administrators 118 via the wide area network 112, via a local area network, and/or via a graphical user interface on a machine configured to execute the database manager 116. The database manager 116 includes a record editor user interface that enables the administrators 118 to edit (e.g. perform a touch-up modification to a record) virtually any piece of data tabled in the medical service provider database 104. By way of a particular example, the database manager 116 is a Web-based application providing database element editing access to authorized administrator. Modifications are initially committed to a production database (not shown) prior to storing on the medical service provider database 104. Examples of editable fields of a provider include, but are not limited to: addresses, hospital affiliations, awards, names, education, specialties and expertise. Examples of information that an administrator cannot edit are: quality scores and provider ratings. Such system calculated values are provided solely by automated computation and updating processes.

Figure 2:
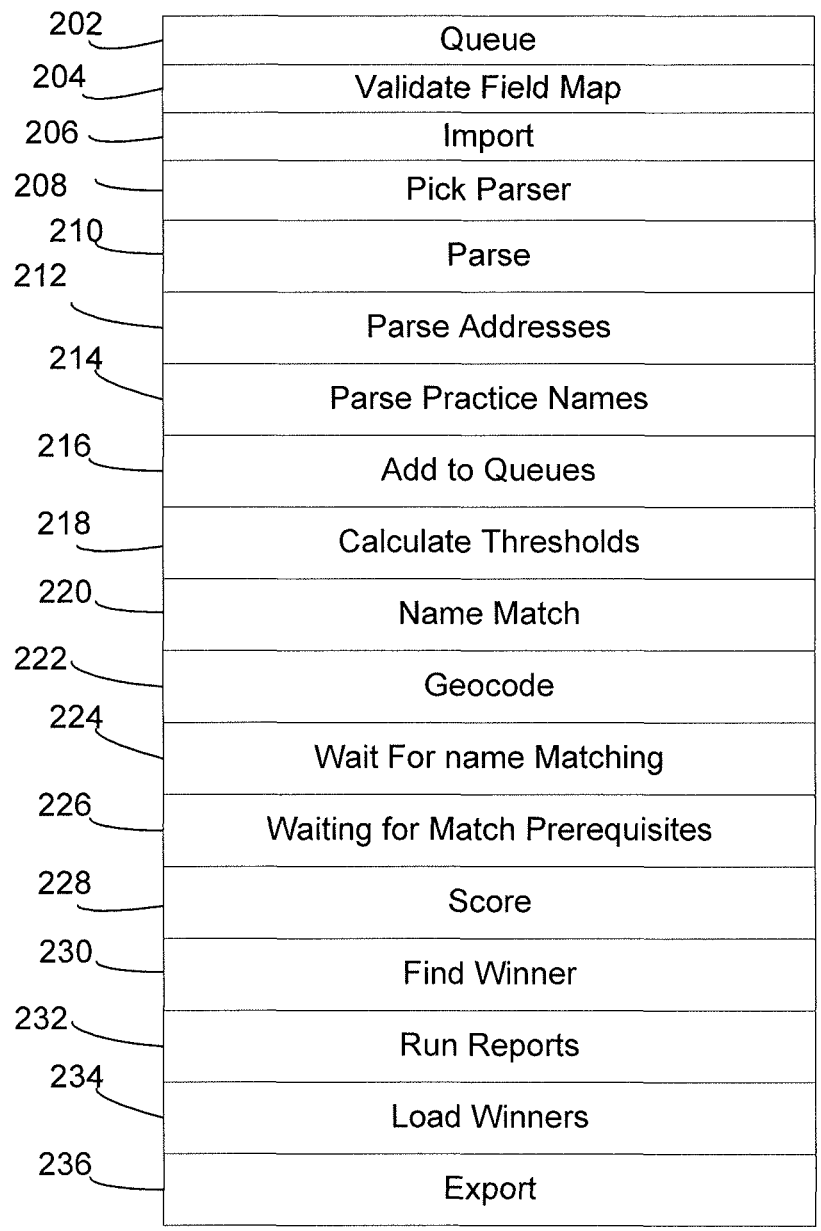
FIG. 2 is a list identifying components (program modules) incorporated within a data record rendering facility for providing normalized medical provider data records from a variety of non-normalized data sources.

Turning to FIG. 2, a set of functions/modules are listed that are provided in the form of computer-executable instructions stored on a non-transitory computer-readable medium. The functions/modules listed in FIG. 2 are accessed and executed by a programmed/programmable processor within the medical service provider data processing engine 100. Each of the identified functions (processes, instances of which are executed by a programmed processor within the data processing engine 100) is applied in sequence upon a particular "resource" that comprises, as described above, a specific batch (iteration) of input data from a data source. However, the functions/modules operate in parallel with regard to individual instances of the resources 102 such that: (1) multiple individual resource instances are processed (or are at least capable of being processed) in parallel by each of the identified functions, and (2) processing of other resource instances is not halted by a disruption in a processing sequence for a particular resource instance. Instead, when a process sequence for a particular resource halts, the processing of other resource instances, by the medical service provider data processing engine 100, may continue executing. A set of exemplary functions/modules executed on the data processing engine 100, for received resources 102, listed in FIG. 2, is described herein below.

A queue 202 receives and identifies a resource instance for processing by the data processing engine 100. The queue 202 thus provides an entry point for the resources 102 into the processing sequence described herein below with reference to FIG. 4.

A validate_field_map 204 analyzes all fields associated with a resource to ensure that all fields in the resource are mapped to a corresponding field of a table in an import tables database of the data processing engine 100. The validate_field_map 204 fails if any fields of the resource are not mapped to a field in the import tables database. When such mapping error arises any one of three potential remedial actions are taken: the field is mapped to an existing field in the import tables, the field is identifies as one that can be ignored (added to "ignored field list" in the data processing engine 100); or a new field type is created (added to "extra field list" in the data processing engine 100). A parser does not currently exist for the case of data designated as "ignored" or "extra" data. However, by placing the data in ignored/extra fields, the information can be identified as being a particular type within the system—instead of discarding the data completely.

An import 206 places the received data into particular buckets for subsequent processing by the system. The input data from resources arrives organized according to defined fields, though the sets of fields may be provided in a variety of forms (i.e. different combinations of data element types), and the import 206 invokes various importers, as needed, for each field in the source data. Upon completion of the import 206 function on a particular resource, the data within the resource is within assigned buckets and ready for further processing by a data type set-specific parser.

A pick_parser 208 executes to automatically (unless a parser match cannot be established) designate one of multiple available executable programmed parsers (see FIG. 3). The pick_parser 208 inspects well-defined sets of data types (fields) contained in the bucketed data rendered by the import 206 (except the ignore and extra tables) to determine which parser, of the available programmed parsers (see FIG. 3), to invoke for processing individual data points (potentially containing multiple pieces of data) within the provided bucket of data. For example, a set of "full addresses" (i.e. all address parts are contained in a single field) is processed by a different parser than a parser that processes segmented address input data where each address component is already separately presented and/or identified in a distinct field. In the case of full addresses, the pick_parser 208 selects a "process_address_full" parser within an address parser class to parse the full address data.

In an exemplary embodiment, parser selections are based on statistical assessment based upon, for example, a quantity of arguments (fields) and identifications of particular types of information contained in one or more of the arguments. Thus, the pick_parser 208 initially compares an argument number to argument numbers for particular parsers. After narrowing the parser options based upon argument number alone, the pick parser compares field types (or combinations of contained fields) associated with the input data points to one or more distinguishing field types associated with a particular parser. Name parser selection differs from other parser types in that number and type of fields is insufficient to ensure selection of a proper field. In the case of name parsers, a particular name processor is selected only if at least 50 percent of the data points can be identified in a census database. This percentage requirement arises from a "pre-matching" operation which merely verifies the existence of at least one instance of the name in the corresponding census database. Designating a parser can be manually specified in a case where no parser has been designated or in a case where a previous automatic selection is to be "overridden" by a manual selection.

A parse 210 invokes a previously selected parser to process previously bucketed data. The resulting parsed data is stored in the parsed data tables.

A parse_addresses 212 is invoked by the parse 210 function. In view of potential data dependencies (an address is often the most important distinguishing identifying piece of information for a received data instance) the parse_addresses 212 function is invoked, if at all, separately before potentially other parsers on related data. During operation of the parse_addresses 212 a match is sought between an input address and a listed address contained in an authoritative address listing. During address parsing, geographic coordinates ("geocodes") are acquired for a provided input address, from a parsed data point, and address candidates from the authoritative address listing. For each candidate address, a minimum distance between the input address and the candidate address is calculated. A score is assigned to each potential address candidate based upon the calculated distance for purposes of selecting a winning address corresponding to the input address.

A parse_practice_names 214 is expressly specified in a sequence of executed functions to ensure that, in view of a data dependency on parsed address data, the parse_practice_names 214 function is executed after the parse_addresses 212 function for a given resource.

An add_to_queues 216 adds data elements that need further post processing (indicated in the parsing results) into an appropriate queue for further processing, including matching and possibly human review. The system creates a queue for each parser, for the purpose of maintaining the information that is parsed along with a count value of how many times the parsed information has been received by the add_to_queues 216. The queued data is then staged for use during later executed matching. The contents of the queue are potentially inspected and processed by human interaction to improve upon later executed matching. For example, a particular specialty is received in a different variation 50 times, but the system does not have the particular variation matched to a currently supported specialty name. If specialty matching algorithms are incapable of matching the specialty with a high degree of certainty, the data will be added to a queue by the add_to_queues 216. Thereafter, the queued data is removed from the queue by a human operator to review and manually match to a known specialty.

The add_to_queues 216 queues data for attaching, to resource data, names for name matching and providing addresses for geocoding.

A calculate_thresholds 218 runs statistical estimates on data to compute whether a process is a success or a failure, and to compute margins of success and failure. The calculate_thresholds 216 gathers metrics on the data processing operation to ensure the automated processing leads to correctly classifying and storing as much of the data as possible. Required passing percentages are manually entered. The thresholds are stored in the configuration database. Thresholds may be set for particular individual source/resource combinations. If the set of data points of the resource cannot meet the threshold, then the entire resource is failed for the particular parser. The failure does not affect any other parsing operations on the resource. By way of example, when parsing a specialty field for a set of data points in a single resource, a threshold of 80 percent is established. This means that 80 percent of the data points within the resource must specify a specialty for which a match exists in the configuration data of the parser (i.e. 80 percent success rate for attempted matches). When a parser fails to achieve the specified threshold, the resource is set aside (failed) for further (manual) processing of the failed parsing. Thus, passing/failing to meet a threshold is on an individual parser operation basis.

A name_match 220 executes logic for rendering name matches for parsed data. The name matching operation is described herein below with reference to FIGS. 4 and 5.

A geocode 222 assigns a geocode to a provided address placed in the geocode 222 function queue by the add_to_queues 216 function.

A wait_for_name_matching 224 executes a wait state function that maintains a particular resource (received data batch) in a wait state while the name_match 220 function completes name matching on the resource.

A waiting_for_match_prerequisites 226 checks the results of previously executed matching operations performed on a particular resource to ensure that relative certainty/reliability of matching results meet specified thresholds. During processing, a statistical majority of failures on a data point causes an error flag to be set to notify an administrator/supervisor of the resource processing to enable correction of a correctable error such as misidentifying a field during mapping, or if the input data itself is incorrect due to a data entry error (e.g. data originally inserted into a wrong field during input at the resource source).

A score 228 executes probabilistic computations on matched data to assign a score representing the degree of certainty that a service provider is properly identified with the processed data.

A find_winner 230 function designates a winning match from a set of potential matches for a particular piece of data for which scores were rendered by the score 228 function. The find_winner 230 function also specifies a winning percentage representing the degree to which the winning match score exceeded a second place match score. A degree of confidence in the winning match increases with increases in winning percentage. Thus, a substantial winning percentage enhances the degree of confidence (e.g. percentage of certainty) that a proper match has been selected, such degree of confidence being a combination of match score(s) and winning percentage(s). An insufficiently high degree of confidence/certainty leads to a match failure, and setting aside the data point value for further, potentially manual processing A run_reports 232 generates reports relating to the results of processing each data point within a processed resource.

A load_winners 234 loads a list of identified medical service providers identified as the winner by the find_winner 230 function.

Figure 4:
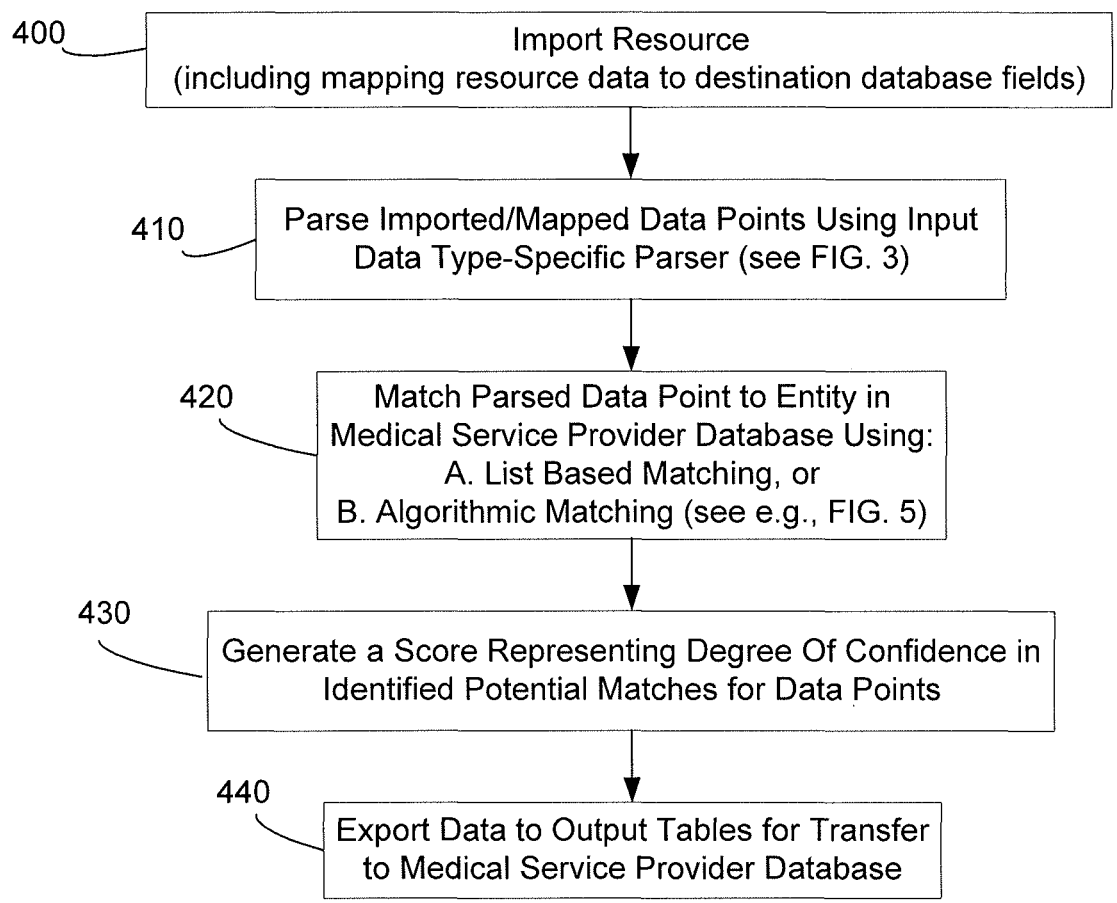
FIG. 4 is a flowchart summarizing a sequence of operations performed to render normalized data records for medical service providers for storage within tables of a medical service provider database accessed by search engine supporting a front-end medical service provider search site.

An export 236 transfers the results of the data processing summarized in FIG. 4 to proper tables within the medical service provider database 104. Once in the tables of the provider database 104, the resource data is available for accessing with other normalized contents of previously processed contents of the resources 102 comprising data from a wide variety of sources.

Turning to FIG. 3, an exemplary set of data type-specific parsers, to which data of a received resource are individually mapped and then processed by one or more data-type specific parser, in accordance with the mapping, are identified. In an exemplary embodiment, each parser has a corresponding parse table that stores parsed data and a matching table containing particularized configuration information for the associated parser.

Actions Parser 302 processes data content describing legal actions that are part of public records.

An Address Insurance Parser 304 processes data content describing the types of insurance (carriers) accepted at an address of a medical service provider.

A Certifications Parser 306 processes data content describing various certifications of an identified medical service provider.

A Credentials Parser 308 processes data content describing the qualifications of an identified medical service provider. During operation of the Credentials Parser 308, a best match is identified between credentials provided in the input data point and an authoritative credential listing (e.g., MD, DO, DDS, DMP, NP, etc.). Relationships between an input credential and a listed credential are scored, including: Credential Match (an exact match) receives a score of +25, Provider Type Credential Match (e.g. DO for MD) receives a score of +15, and Provider Type Credential Mismatch (e.g., DO for NP) receives a score of −25. The scores are used in conjunction with other match scores to determine an overall match between an entity identified in the input data and a provider entity listed in an authoritative listing of providers.

A Dates Parser 310 processes data content describing a calendar date. The dates processor converts all formats of input date information into month, date, year form. Thus, 10/14/94 would be understood by the parser to be Oct. 14, 1994.

An Expertise Parser 312 processes data content identifies an area of expertise of an identified medical service provider.

A Hospitals Parser 314 processes data content specifying a hospital name to render additional information that may be deduced from the full hospital name, such as a geographic location. For example, a hospital string "Memorial Hospital of New York" is recognized by the Hospitals Parser 314 as the name of a geographic location (city or state). Thus, based upon the operation of the Hospitals Parser 314, the system may be able to obtain a location (if no address was provided) with a higher degree of certainty than use of text strings alone. Hospitals Parser 314 therefore seeks to apply various data extraction heuristics to Hospital names to render a resulting data set that goes beyond merely reciting a string of text (i.e., the original hospital input name). This added information provides additional certainty when a match is sought between the hospital name text string and an authoritative listing of hospital names.

An Hours Parser 316 processes data content describing office hours of an identified medical service provider.

An Image Parser 318 processes data content describing an image (e.g. a photo) of an identified medical service provider.

An Insurance Parser 320 processes data content describing general insurance information of an identified medical service provider.

A Language Parser 322 processes data content describing languages by which patients can communication with an identified medical service provider.

A Licenses Parser 324 processes data content describing medical licenses held by an identified medical service provider. During operation of the Licenses Parser 324, a best match is identified between a piece of provided license information in the input data point and an authoritative license listing (e.g., NPI, UPIN, State board, etc.). Relationships between an input license and a listed license are scored, including: License type unknown that receives a score of −5, License Type Match that receives a score of 10, License Match that receives a score of 50, Partial License Match that receives a score of +25, and License Mismatch that receives a score of −50. The scores are used in conjunction with other match scores to determine an overall match between an entity identified in the input data and a provider listed in an authoritative listing of providers.

A Names Parser 326 processes data content describing the full name, including title, of an identified medical service provider.

A Phones Parser 328 processes data content describing the phone numbers of an identified medical service provider.

A Practice Names Parser 330 processes data content describing a name, if any, of an affiliated practice group of an identified medical service provider.

A Provider Parser 332 processes data content describing data such as gender, birth date information, etc. of an identified medical service provider.

A Schools Parser 334 processes data content describing the professional schools (medical, dental, etc.) attended by an identified medical service provider, or any other school relationship associated with the identified medical service provider (e.g. teacher, lecturer, etc.).

A Specialties Parser 336 processes data content describing areas within which an identified medical service provider is associated. The Specialties Parser 336 includes a specialties matching function that compares a specified specialty from a data point instance to an authoritative listing of specialties, including a categorization (hierarchy) of specialties, to find and score a match between the specified specialty and a specialty within the authoritative listing of specialties. In addition to parent-child/general-specific specialty relationships, the authoritative listing also groups similar specialties. When the Specialties Parser 336 seeks to match the specified specialty to one of the ones listed in the authoritative listing of specialties, the following match types are considered for purposes of scoring a match and then selecting a winning match between the specified specialty and one listed in the authoritative listing of specialties. A "specialty match" is a direct match between the specified specialty and one listed in the authoritative listing and receives a score of +25. A "specialty mismatch" on the other hand receives a score of −25. A "parent_specialty match" is a match between a generalized version of the specified specialty (e.g. pathology for anatomic pathology) and receives a score of +20. A "specialty similar level 1" is assigned to a match between a specified specialty and a specialty that is sufficiently general to encompass the specified specialty (e.g. Internal Medicine for Obstetrics & Gynecology) and receives a score of 22. A "specialty similar level 2" is assigned to a match between and specified specialty and a specialty that fits at least partially within a specialty within the authoritative listing (e.g. Obstetrics & Gynecology and Gynecology/Oncology) and receives a score of 15. The Specialties Parser 336 completes processing of the specified specialty by identifying a specialty listed in the authoritative listing for which a highest match score was obtained during match scoring.

A Training Parser 338 processes data content describing the experience and training of an identified medical service provider.

An Associations Parser 340 processes data content describing a professional association of which the identified medical service provider is a member.

It is noted that the above list of parsers executed within the data processing engine 100 is not exhaustive, and thus additional parsers are contemplated to handle other data types (including high level parsers for handling composite data blobs, that invoke data-type specific parsers when certain types of data are recognized within the composite data blobs).

In the course of describing certain parsing functions (e.g., parse addresses 212 and parse practice names 214 functions), a "data dependency" was introduced. Particular examples of such data dependencies, and their resolution, are described herein below.

Some data points (comprising multiple fields of related data) contain related information within strings that have not yet been parsed. The certain helper parsers operate as helpers to better understand the data contained within a particular data point currently being processed by another parser. For example, during address parsing a parser may encounter a blob of text that contains data points that need to be processed by other, data type-specific, parsers. For example, the parse addresses 212 parser invokes helper parsers, such as the phones 328 parser, the practice names 330 parser, the hours 316 parser, and the address insurance 304 parser to get the most out of the string. The invoked helper parsers address particular parts of the content within the data point currently being processed. Moreover, data dependency also arises in the context of taking parsed and understood data obtained during exporting and data loading (into the medical service provider database 104) to deduce relationships and further enhance the data.

The following are examples of data dependencies that arise during processing resource data:

a) Resource has name data and nondescript school data:

Name: John Smith MD

School: Harvard

During name processing, a title of MD is understood to identify a doctor. During school processing, the knowledge of John Smith being an MD is leveraged to complete the school name "Harvard Medical School." Similarly, a title of DDS causes the school name to be completed as "Harvard Dental School."

b) Provider practicing address provided with nondescript hospital data:

Practice address: 124 Main St, Hudson MA

Hospital affiliation: Saint Vincent's Hospital

During address processing, the general geographic area where the doctor practices, and most likely resides is understood to be within a reasonable distance of the doctor's practice address. Therefore, during hospital affiliation processing, Saint Vincent's Hospital is looked up, and it is determined that only one exists in the general geographic region (e.g. in the state of Massachusetts). The known information for Saint Vincent's Hospital indicates that it is in Worcester MA, and as a result the full address information for that particular hospital instance is added to the previously incomplete address information for the affiliated hospital. If more than one match was found based on all practicing addresses, then the address will remain unresolved (unmatched) after processing is complete.

c) License data provided along with nondescript provider name

License: A201701, CA

Name: Xander Haris

During License processing by the licenses parser 324, the license identification is determined to be a California Dental License. Using this information, the name Xander Haris is deduced to be a dentist despite not being given an explicit title in the input Name field. The name Xander Haris is completed by the parser by adding the title of DDS deduced from the information rendered by the licenses parser 324.

d) Association provided but no explicit practicing specialty is given.

Association: American Board of Internal Medicine

During association parsing by the Associations parser 340, the association identification may be leveraged to identify an area of specialization of the identified medical service provider. Based upon the identification of "American Board of Internal Medicine" the identified medical service provider is identified as specializing in "internal medicine."

Turning to FIG. 4, a sequence of operations carried out on a received instance of the resources 102 is summarized. Initially during an import resource 400 stage a received resource (of resources 102) containing multiple data points, is digested and filtered to render data points assigned to particular data type-specific buckets. During the import resource 400, stage data points within the queued resource (see queue 202) are placed within buckets according to the data type of the data point. During the import resource 400 stage, a mapping is created between individually identifiable parts (e.g. fields of data points) of the queued resource and normalized data types handled by the parsers (see FIG. 3) of the medical service provider data processing engine 100. For example, a received data file includes a data record format including a field called "Address_Line_1" that is mapped during the mapping operation of the import resource 400 stage an "address_line1" field in an address import table within the data processing engine 100. Thus, the mapping operation configures automated processing of pieces of received data notwithstanding the existence of differences between field names assigned to the data by the resource and the provider data processing engine 100. Once the mapping is completed for the identified field name of the queued resource, the data processing engine 100 can convert the input data without human intervention for all instances of that particular identified field in the queued resource.

Next, during a parsing 410 stage, the data processing engine 100 invokes particular ones of the parsers enumerated in FIG. 3 to digest the content of data points previously assigned to particular data-type buckets during the import resource 400 stage. During the parsing 410 stage, the pick parser 208 function runs through the bucketed imported data points, one data (bucket) type at a time, and designates a parser, from the set of supported parsers enumerated in FIG. 3, to parse (i.e. digest to individual record field data storable in the medical provider database 104) the contents of the fields within data points within each particular bucket.

Upon completion of the parsing 410 stage wherein the appropriate data type parsers and specified functions process the previously bucketed import data, results are tabulated in temporary database tables maintained by the provider data processing engine. Thus, the parsing 410 stage breaks the bucketed data, which may still be in relatively unstructured form (including strings comprising multiple types of field data), into understandable atomic data for further analysis by the data processing engine (including matching stage 420) and storage upon the provider database 104. For example, names that come in as one string like John A. Smith are parsed into their first, middle, and last components of first name: John, middle initial: A., and last name: Smith.

Next, during a matching 420, the data processing engine seeks to identify a particular service provider entity to which the parsed data corresponds. In accordance with an illustrative example, during the matching 420, a number of potential matches are identified, and thereafter a best match is determined from the set of potential matches. During the matching 420 stage, the parsed data is compared to entries of authoritative data listings (e.g. as official lists of medical service provider specialties, hospitals, US cities, etc.). During the matching 420 various matching algorithms are potentially employed based upon the data type of a particular data point currently being processed. In an illustrative example, two types of matching approaches are supported: (1) list based, and (2) algorithmic. Both approaches are described herein below.

A. List Based Matching

During list based matching, parsed data strings (data points) are compared to an authoritative list using knowledge of the data points, to identify a set of potential matches. For example, when matching a hospital an attempt is initially made to identify any recognized abbreviations, such as Hosp. or Ctr., to normalize the data as much as possible. City and state information that may have been parsed out of the initial string (e.g. "Memorial Hospital of New Jersey") is re-introduced for purposes of carrying out a match search. Lastly, a possible state is considered based upon other addresses received within the resource containing the data point of interest. With this data in hand, the matching 420 invokes a variety of matching scenarios (resulting in possibly different matching entity from the authoritative list) and calculates a score for each scenario. Finally, the data processing engine 100 compares all the calculated scores from the various scenarios and returns the best match score as the winner (see Find Winners 234). By way of example, list based matching is employed to identify a match for: Hospitals, Specialties, Languages, Schools, Trainings, Expertise, and Insurance. The input data is not modified to perform a match. However, the type/closeness of a match is considered to determine a best match.

B. Algorithmic Matching

During Algorithmic matching, data points which cannot be put into a list (and thus cannot be processed using the above-described list based matching approach) are subjected to various algorithms to render a match score and select a best match to existing data. By way of example, the data point data from the received resource is matched to data from another source. Algorithmic Matching is used, for example, to match a received provider name string to an existing name string. Algorithmic matching of provider name strings includes three distinct components: Filtering, Identifying, and Analyzing.

During filtering, the data processing engine 100 breaks up a name specified in a data point into constituent parts, performs transformations on the constituent parts to identify a match between the transformed name versions and a name from an authoritative name listing. The resulting matches are scored and only the highest scored transformations are considered as potential name matches. Using the filtered results, the name matching process identifies more information about the names of the current data point and the names to which the current name data point is being compared. This information can be middle names, potential nicknames used, whether the first name is a single initial, etc. After identifying addition information to aid the matching process, metadata for the name data point's identified components are run through analysis which attempts various combinations of transformed name parts (first, middle, last and suffix) and scores each name transformation combination appropriately. Scores are tallied up and a best match (or set of top ranked matches) is returned.

An exemplary algorithmic name matching and scoring operation executed by the data processing engine 100, is described herein below. The algorithmic name matching and scoring operation is configured to: (1) generate a set of name transformation combinations (including no transformation), (2) compare each name transformation combination to an authoritative listing of provider names to identify a set of name transformation combinations matching a name in the authoritative listing, and (3) apply a match scoring criterion, assigning score values to particular characteristics of each potential match, to render an overall score indicative of a level of confidence in the particular match between the transformed name and an entry in the authoritative listing. The thoroughness of both the transformation combination comparisons and the match scoring criterion ensure a high degree of confidence in a resulting name match selection, even when multiple potential name matches are initially identified. Ensuring a high degree of certainty in name matching ensures that associated provider data is associated with a correct provider identified in the provider database 104.

Figure 5:
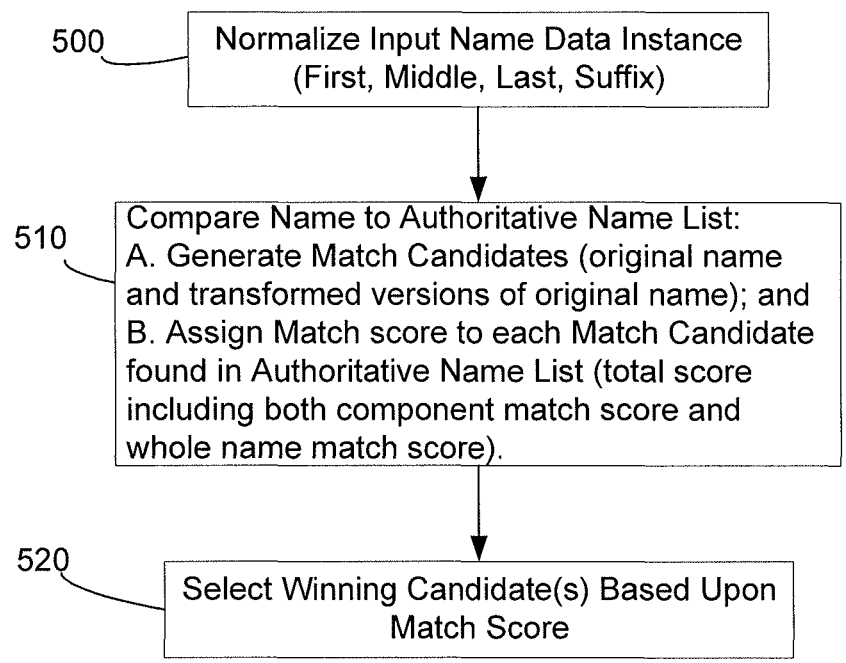
FIG. 5 is a flowchart summarizing a sequence of operations performed to render an algorithmic name match based upon scored comparisons of input data point value transformations that match authoritative listing entries.

Turning to FIG. 5, by way of a particular example of the above-described name matching and scoring operation, an exemplary algorithmic name matching and scoring operation (described by way of a detailed example below) is carried out, by a compare names function, on an instance of input name data contained within a received data point. During 500, the compare names function initially normalizes the name input by first characterizing an input name string or strings. Examples of such name string formats include: (1) Split String, comprising first, middle, last, and suffix separated into distinct fields, and (2) Full String, comprising a single string containing the full name. Full String, in turn, is distinguished by content as follows: first-middle-last, first-last, and first-middle_initial-last. Handlers are provided to convert each of the Full String types into the split string format. Additional functions, performed by the compare names function on the normalized data of the input name instance, are described herein below.

During a comparing stage 510 the compare names function carries out name matching operations between an authoritative listing of names and a set of name match candidates rendered by performing various transformations (described below) on components of the normalized input name. The rendered name match candidates are compared both as individual components and as a whole and match types (described below) are scored. Each name match candidate (including the original input name) is assigned an overall match score based upon the match types on the individual parts of the name and the name as a whole.

During 520 the compare names function selects a winning candidate or candidates based upon a ranking of the overall match scores for candidate names rendered during the comparing stage 510. The winning candidate is determined by the highest overall match score among the candidates for which a match was found during the comparing stage 510.

The various transformations on constituent parts of the normalized input name, to render candidate names for comparison to the authoritative listing of provider names, are described herein below.

A Score Name Suffix operation carries out transformations on the suffix field of the normalized input name data instance. If a suffix is present, the Score Name Suffix operation translates the suffix string (e.g. Sr., Jr., II, III, etc.) into a corresponding integer value. In a particular example, Jr. and II are translated into the integer value '1' for purposes of executing a comparison to an authoritative set of names.

A Score Last Name operation carries out transformations on the last name field of the normalized input name data instance. Before commencing comparison and scoring, the Score Last Name operation analyzes a last name instance to determine whether the name includes multiple parts (e.g. Hill-Jones). If the last name contains multiple parts, then the parts are each processed separately. Thus rendering multiple match results. Multiple name transformations are applied on the last name to render (candidate) input for a subsequent comparison to the names within the authoritative database. Such transformations include ones rendered by the following algorithms: metaphone (similar sound/different letters), nysiis, and fuzzy (e.g. Levenshstein distance algorithm which detects typographical errors including: transposition, insertion, deletions, and substitutions). The results of the Score Last Name will include potentially multiple parts, based upon whether the last name contained multiple parts. In the case of multi-part last name, the result of the last name match will identify whether the selected (best) match was from a first part, second part, or both parts of the multi-part last name.

A Score First Name operation carries out transformations on the first name field of the normalized input name data instance. Before commencing comparison and scoring, the Score First Name operation analyzes a first name instance to determine whether the name includes multiple parts (e.g. Michael-Jessie). If the first name contains multiple parts, then the parts are each processed separately. Thus rendering multiple match results. Multiple name transformations are applied on the first name to render input for a subsequent comparison to the names within the authoritative database. Such transformations include ones rendered by the following algorithms: metaphone, nysiis, fuzzy (e.g. Levenshstein distance), nickname (using a compilation of known nick names), truncation, and initials (first name solely provided in form of an initial). The results of the Score First Name will include potentially multiple parts, based upon whether the first name contains multiple parts. In the case of a multi-part first name, the result will identify whether the match was from a first part, second part, or both parts. Additionally, the matching and scoring of a first name for a multi-part first name includes a swapping the order of the parts transformation and performing a comparison to the authoritative database to see whether the swapping parts transformation of the input first name results in a match. In that case, the result will identify the matched name arising from swapping first and second parts as well as a score for the match.

A Score Middle Name operation carries out transformations on the middle name field of the normalized input name data instance. The operation of the Score Middle Name operation is the same as the Score First Name operation described above, and therefore will not be repeated.

A Score Whole Name operation carries out a comparison and scoring function on the entire name input. The Score Whole Name operation performs transformations on the input string, including: metaphone, nysiis, and fuzzy. The Score Whole Name operation provides yet another way to ensure that a group of related input data, including a provider name, is properly assigned to an entity in the provider database 104 when processing is complete and the results are exported to the provider database 104.

The "scoring" of matches has been mentioned above in the context of matching candidate names for an input name string contained within a parsed data point, including candidate names containing transformed constituent parts, to entries in an authoritative name listing. There are several ways in which to perform match scoring, and an example of match scoring is provided below. In the exemplary embodiment, for each candidate name compared to a potential match candidate, the type of match for each one of the constituent parts (based upon the transformation resulting in the match) and the name taken as a whole, is scored. The scores assigned to the matches for constituent parts (e.g. first, middle, last, and suffix) and the overall name are summed to render an overall match score for the particular candidate name. When all the comparisons have been scored, the results are reviewed to identify a top scoring candidate match (or matches). In the illustrative example, each "scored" match type is stored as an attribute on the attempted match. The list of match types is listed below.

The following is a listing of exemplary match types, and associated scores, arising from comparing various transformations of an input name (including both non-transformed and transformed versions) and an authoritative listing of names.

EXACT_STRING_MATCH, assigned a score of +25, is a match that occurred without any transformation of the compared string.

METAPHONE_MATCH, assigned a score of +6, is a match that occurred as a result of performing a metaphone transformation of the compared string.

NYSIIS_MATCH, assigned a score of +6, is a match that occurred as a result of performing an nysiis transformation of the compared string.

FUZZY_MATCH, assigned a score of +6, is a match that occurred as a result of performing a fuzzy logic-based transformation of the compared string.

INITAL_MATCH, assigned a score of +20, is a match to either the first or middle name field that occurred as a result of performing, for a whole name where the last name matches, a comparison a provided initial to a first letter of a compared name. For each matching initial (e.g. a match occurs if the initial in the input name is replaced by a corresponding full name containing the same first letter) a value of +20 is scored in the name field. Thus, an input name of James T Jones would have a +20 value assigned to the middle initial field based upon an "initial match" with an entry in the authoritative listing of James Tiberius Jones. In the case of J T Jones, +20 values would be assigned to both the first and middle name fields in view of an initial match with James Tiberius Jones.

ONE_TO_ONE, assigned a score of 0, is true when the candidate name and compared name have only one name in the constituent name field.

ONE_TO_TWO, assigned a score of −3, is true when one of the candidate and compared name field has a different number of name elements than the other.

TWO_TO_TWO, assigned a score of 0, is true when the candidate name and compared name have two names in the constituent name field.

TWO_TO_TWO_MIXED, assigned a score of −5, is true when the candidate name and compared name both have two names, but it is necessary to switch the order of the two names in the original to render a matching candidate name field.

ONE_MIDDLE_EMPTY, assigned a score of +15 for the entire name, is true when a match occurred after specifying the middle name as being empty (to match an empty field specified in the other compared name).

BOTH_MIDDLE_EMPTY, assigned a score of +20 for the entire name, is true when both the original name and compared name in the authoritative name listing are empty.

BOTH_SUFFIX_EMPTY, assigned a score of +5 for the suffix component, is true when both the original name and compared name in the authoritative name listing do not specify a suffix.

ONE_SUFFIX_EMPTY, assigned a score of +0 for the suffix component, is true when one of the original name and compared name in the authoritative name listing does not specify a suffix.

BOTH_SUFFIX_SET, assigned a score of +10 for the suffix component, is true when both the original name and compared name in the authoritative name listing specify a suffix.

FIRST_MIDDLE_SWAPPED, assigned a score of −25, is true when a match occurs after swapping the names within the first and middle fields to render a match.

TRUNCATE_MATCH, assigned a score of +22, is a match that occurred as a result of performing a truncation transformation of the compared string.

NICKNAME_MATCH, assigned a score of +23, is a match that occurred as a result of performing a nickname substitution of the compared string.

With continued reference to the description of FIG. 4, during a scoring 430 stage, all available data relating to the previously executed matching 420 is gathered, and the medical service provider data processing engine 100 attempts to match an identified entity (based upon the best match score during matching 420) to an identified entity that exists within the medical service provider database 104. For example, during scoring 430 the data processing engine 100 takes an instance of data linked to a particular John Smith, and with a specified degree of certainty (represented by an assigned match "score") states that the John Smith in question is the one identified in the database 104 as the one residing in New York, is a doctor, and practices Internal Medicine. To do this, match scores previously generated during the matching 420 stage are used as data points and a percent of certainty is calculated. In illustrative examples, unless a particular identity is assigned to data with a very high degree of certainty (e.g. higher than 99.99%) the data point will not be committed to the database 100.

During an export stage 440, the data points of the resource that have been matched to a high degree of certainty to an existing medical service provider entity, are written to a set of export tables broken up by data types maintained by the medical service provider data processing engine 100. Once the digested, normalized, and verified data is committed to the export tables of the data processing engine 100, the data is ready for export to the database 104. In general, once the data has been committed to the export tables of the data processing engine 100, the data is ready for storage in a searchable database by any search engine, such as the medical service provider search engine 114.

In a particular illustrative example, during the export step product-specific processes are executed to ensure that the data that is in the final export tables, per data point, are in the format that can be consumed by the product. Several business rules are applied to the data points rendered from the imported resource to ensure the data is ready for consumption by an intended front-end query engine and user interface through which searches are submitted and results are thereafter presented. By way of example, business-specific rules are applied to ensure:

a) Assigning IDs to data points such as specialties, expertise, hospitals, schools, and other such lookup tables to enable consuming processes to simply take the IDs and assign them appropriately.

b) Assigning provider IDs if they were specifically loaded during received resource processing. This is especially used by external processes which have already matched the provider to an existing database (via, for example, a provider_id field) so that all the parsed data can be assigned to the provider. This eliminates the potential for matching to someone other than the one intended provider.

c) Bucketing data into their individual tables and creating views which act as interfaces to the clean data.

d) Using other parsed data points, other deductions can be made about other data points that may not have enough information available during parsing to resolve. Examples of such data were discussed herein above with regard to the "data dependencies" processing.

All references, including publications, patent applications, and patents, cited herein are hereby incorporated by reference to the same extent as if each reference was individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for transforming, by a computer system configured to implement a medical service provider data processing engine including a processor and computer-readable medium including computer-executable instructions, received input medical service provider data records from a variety of medical service provider data sources into standardized medical service provider data records for storage on a medical service provider database for access and use by a medical service provider search engine associated with a search site for searching a population of medical service providers represented by data record elements in the medical service provider database, the method comprising:

importing, by the data processing engine, a received resource containing multiple data points for a medical service provider population, wherein during the importing, the received resource is digested to render a mapping between an individually identifiable part of a data point instance of the multiple data points for a medical service provider population and a corresponding normalized data type of a set of normalized data types handled by a set of data type-specific parsers configured on the data processing engine;

designating, based upon the mapping by the data processing engine during the importing, one of the data type-specific parsers for each individually identifiable part of a data point instance of the multiple data points for a medical service provider population;

parsing, by the data processing engine after the designating, individually identifiable parts of the data point instances of the multiple data points using corresponding designated ones of the set of data-type specific parsers to render a set of parsed data points for a medical service provider population;

matching, by the data processing engine, individual ones of the set of parsed data points for a medical service provider population to multiple listing entries of an authoritative data listing, wherein, during the matching, an algorithmic matching operation is performed for a parsed data point instance of the set of parsed data points for a medical service provider population, wherein the algorithmic matching operation comprises performing for each one of the set of parsed data points for a medical service provider population:

generating a set of transformed data points by applying a set of transformation types to the parsed data point instance, and identifying a set of algorithmic matches between the set of transformed data points and corresponding listing entries of the authoritative data listing;

rendering a set of transformation match scores by assigning an algorithmic match score to each match between a one of the set of transformed data points and a listing entry of the authoritative data listing, wherein the algorithmic match score for a particular one of the set of transformed data points is based upon a type of transformation performed on the parsed data point instance to render the particular one of the set of transformed data points;

determining, by the data processing engine, a highest match score of the set of transformation match scores; and exporting the particular one of the set of transformed data points, corresponding to the highest match score, to the medical service provider database.

2. The method of claim 1 wherein the algorithmic match is carried out during a name matching operation for a medical service provider entity.

3. The method of claim 1 wherein the algorithmic match is carried out during a specialties matching operation for a medical service provider entity.

4. The method of claim 1 wherein the algorithmic match is carried out during a credentials matching operation for a medical service provider entity.

5. The method of claim 1 wherein during the parsing, a helper parser is invoked to extract supplemental data from a data point field differing from a data point field currently being processed by a designated parser for a data point of the multiple data points.

6. The method of claim 5, wherein the helper parser provides information for completing a school name based upon provider title information.

7. The method of claim 5, wherein the helper parser provides information for completing a hospital name based upon a provider practice address.

8. The method of claim 5, wherein the helper parser provides information for completing a provider entity title based upon a provider license string.

9. The method of claim 5, wherein the helper parser provides information for completing practice specialty based upon provider associations.

10. A non-transitory computer-readable medium including computer-executable instructions for transforming, when executed on a computer system configured to implement a medical service provider data processing engine, received input medical service provider data records from a variety of medical service provider data sources into standardized medical service provider data records for storage on a medical service provider database for access and use by a medical service provider search engine associated with a search site for searching a population of medical service providers represented by data record elements in the medical service provider database, the computer-executable instructions, when executed on the computer system, facilitating performing a method comprising:
   importing, by the data processing engine, a received resource containing multiple data points for a medical service provider population, wherein during the importing, the received resource is digested to render a mapping between an individually identifiable part of a data point instance of the multiple data points for a medical service provider population and a corresponding normalized data type of a set of normalized data types handled by a set of data type-specific parsers configured on the data processing engine;
   designating, based upon the mapping by the data processing engine during the importing, one of the data type-specific parsers for each individually identifiable part of a data point instance of the multiple data points for a medical service provider population;
   parsing, by the data processing engine after the designating, individually identifiable parts of the data point instances of the multiple data points using corresponding designated ones of the set of data-type specific parsers to render a set of parsed data points for a medical service provider population;
   matching, by the data processing engine, individual ones of the set of parsed data points for a medical service provider population to multiple listing entries of an authoritative data listing, wherein, during the matching, an algorithmic matching operation is performed for a parsed data point instance of the set of parsed data points for a medical service provider population, wherein the algorithmic matching operation comprises performing for each one of the set of parsed data points for a medical service provider population:
      generating a set of transformed data points by applying a set of transformation types to the parsed data point instance, and
      identifying a set of algorithmic matches between the set of transformed data points and corresponding listing entries of the authoritative data listing;
   rendering a set of transformation match scores by assigning an algorithmic match score to each match between a one of the set of transformed data points and a listing entry of the authoritative data listing, wherein the algorithmic match score for a particular one of the set of transformed data points is based upon a type of transformation performed on the parsed data point instance to render the particular one of the set of transformed data points;
   determining, by the data processing engine, a highest match score of the set of transformation match scores; and
   exporting the particular one of the set of transformed data points, corresponding to the highest match score, to the medical service provider database.

11. The non-transitory computer-readable medium of claim 10, wherein the algorithmic match is carried out during a name matching operation for a medical service provider entity.

12. The non-transitory computer-readable medium of claim 10, wherein the algorithmic match is carried out during a specialties matching operation for a medical service provider entity.

13. The non-transitory computer-readable medium of claim 10, wherein the algorithmic match is carried out during a credentials matching operation for a medical service provider entity.

14. The non-transitory computer-readable medium of claim 10, wherein during the parsing, a helper parser is invoked to extract supplemental data from a data point field differing from a data point field currently being processed by a designated parser for a data point of the multiple data points.

15. A system for transforming received input medical service provider data records from a variety of medical service provider data sources into standardized medical service provider data records for storage on a medical service provider database for access and use by a medical service provider search engine associated with a search site for searching a population of medical service providers represented by data record elements in the medical service provider database, the system comprising:
   a programmed processor; and
   a non-transitory computer readable medium including computer-executable instructions for configuring the programmed processor to implement a medical service provider data processing engine, the computer-readable medium including computer-executable instructions for facilitating, when executed by the programmed processor:
      importing, by the data processing engine, a received resource containing multiple data points for a medical service provider population, wherein during the importing, the received resource is digested to render a mapping between an individually identifiable part of a data point instance of the multiple data points for a medical service provider population and a corresponding normalized data type of a set of normalized data types handled by a set of data type-specific parsers configured on the data processing engine;

designating, based upon the mapping by the data processing engine during the importing, one of the data type-specific parsers for each individually identifiable part of a data point instance of the multiple data points for a medical service provider population;

parsing, by the data processing engine after the designating, individually identifiable parts of the data point instances of the multiple data points using corresponding designated ones of the set of data-type specific parsers to render a set of parsed data points for a medical service provider population;

matching, by the data processing engine, individual ones of the set of parsed data points for a medical service provider population to multiple listing entries of an authoritative data listing, wherein, during the matching, an algorithmic matching operation is performed for a parsed data point instance of the set of parsed data points for a medical service provider population, wherein the algorithmic matching operation comprises performing for each one of the set of parsed data points for a medical service provider population:

generating a set of transformed data points by applying a set of transformation types to the parsed data point instance, and identifying a set of algorithmic matches between the set of transformed data points and corresponding listing entries of the authoritative data listing;

rendering a set of transformation match scores by assigning an algorithmic match score to each match between a one of the set of transformed data points and a listing entry of the authoritative data listing, wherein the algorithmic match score for a particular one of the set of transformed data points is based upon a type of transformation performed on the parsed data point instance to render the particular one of the set of transformed data points;

determining, by the data processing engine, a highest match score of the set of transformation match scores; and exporting the particular one of the set of transformed data points, corresponding to the highest match score, to the medical service provider database.

16. The system of claim 15, wherein the algorithmic match is carried out during a name matching operation for a medical service provider entity.

17. The system of claim 15, wherein the algorithmic match is carried out during a specialties matching operation for a medical service provider entity.

18. The system of claim 15, wherein the algorithmic match is carried out during a credentials matching operation for a medical service provider entity.

19. The system of claim 15, wherein during the parsing, a helper parser is invoked to extract supplemental data from a data point field differing from a data point field currently being processed by a designated parser for a data point of the multiple data points.

20. The system of claim 15 wherein the generating a set of transformed data points by applying a set of transformation types to the parsed data point instance includes applying a fuzzy transformation.

* * * * *